(12) United States Patent
Shapland et al.

(10) Patent No.: US 8,152,786 B2
(45) Date of Patent: Apr. 10, 2012

(54) COLLECTION CATHETER AND KIT

(75) Inventors: James Edward Shapland, Vadnais Heights, MN (US); Tuan Minh Doan, Burnsville, MN (US); Mark Francis Brown, New Hope, MN (US)

(73) Assignee: Osprey Medical, Inc., St. Paul, MN (US)

( * ) Notice: Subject to any disclaimer, the term of this patent is extended or adjusted under 35 U.S.C. 154(b) by 1150 days.

(21) Appl. No.: 11/557,312

(22) Filed: Nov. 7, 2006

(65) Prior Publication Data

US 2008/0108960 A1 May 8, 2008

(51) Int. Cl.
*A61M 1/00* (2006.01)
*A61M 37/00* (2006.01)

(52) U.S. Cl. ........ 604/321; 604/317; 604/320; 604/508; 604/509; 604/4.01; 604/6.16; 604/27; 604/28; 604/544; 606/108; 606/127; 606/159; 606/191; 623/1.23; 623/1.3; 623/3.1

(58) Field of Classification Search .......... 604/4.01, 604/6.16, 27–28, 544, 321, 320, 317, 508, 604/509; 606/108, 127, 159, 191; 623/1.23, 623/1.3, 3.1
See application file for complete search history.

(56) References Cited

U.S. PATENT DOCUMENTS

| | | | |
|---|---|---|---|
| 4,054,137 A | | 10/1977 | Lee et al. |
| 4,581,017 A | * | 4/1986 | Sahota ................. 604/101.01 |
| 6,080,170 A | * | 6/2000 | Nash et al. ................. 606/159 |
| 6,500,158 B1 | | 12/2002 | Ikeguchi |
| 6,554,819 B2 | | 4/2003 | Reich |
| 7,331,922 B2 | | 2/2008 | Mohl |
| 7,722,596 B2 | * | 5/2010 | Shapland et al. ............ 604/509 |
| 2002/0099254 A1 | | 7/2002 | Movahed |
| 2002/0165598 A1 | * | 11/2002 | Wahr et al. ................. 623/1.11 |
| 2003/0191434 A1 | * | 10/2003 | Dorros et al. ............ 604/101.04 |

(Continued)

FOREIGN PATENT DOCUMENTS

| | | |
|---|---|---|
| WO | WO 89/01309 | 2/1989 |
| WO | WO 01/83004 A1 | 11/2001 |
| WO | WO 02/060511 A2 | 8/2002 |
| WO | WO 02/087677 A2 | 11/2002 |

(Continued)

OTHER PUBLICATIONS

Michishita, et al. "A Novel Contrast Removal System From the Coronary Sinus Using an Absorbing Column During Coronary Angiography in a Porcine Model", *Journal of the American College of Cardiology*, vol. 47, No. 9 (2006).

(Continued)

*Primary Examiner* — Tatyana Zalukaeva
*Assistant Examiner* — Ginger T Chapman
(74) *Attorney, Agent, or Firm* — Merchant & Gould P.C.

(57) ABSTRACT

A catheter for collecting fluid such as blood from a vessel such as a coronary sinus of a patient has an elongated, flexible tubular portion and an annular sealing member spaced from a distal end of the tubular member. A proximal end of the tubular member is adapted to be connected to a source of suction for applying suction to a collection lumen of the tubular member. The distal end is placed in a blood vessel with the sealing member spaced from opposing surface of the vessel in an absence of a suction applied to the collection lumen. Suction is applied to the collection lumen in an amount sufficient to draw blood from the vessel through the fluid inlet and into the collection lumen and further sufficient to urge the opposing surface of the vessel to migrate into sealing engagement with the sealing member.

7 Claims, 4 Drawing Sheets

U.S. PATENT DOCUMENTS

| | | | |
|---|---|---|---|
| 2003/0236533 A1* | 12/2003 | Wilson et al. | 606/127 |
| 2004/0102766 A1 | 5/2004 | Poleo, Jr. | |
| 2004/0254523 A1* | 12/2004 | Fitzgerald et al. | 604/21 |
| 2005/0124969 A1 | 6/2005 | Fitzgerald et al. | |
| 2005/0256441 A1 | 11/2005 | Lotan et al. | |
| 2006/0013772 A1 | 1/2006 | LeWinter et al. | |
| 2007/0118072 A1* | 5/2007 | Nash | 604/35 |
| 2009/0069829 A1* | 3/2009 | Shturman | 606/159 |
| 2010/0082004 A1* | 4/2010 | Shapland et al. | 604/321 |

FOREIGN PATENT DOCUMENTS

| | | |
|---|---|---|
| WO | WO 2005/082440 A1 | 9/2005 |
| WO | WO 2006/042219 A2 | 4/2006 |

OTHER PUBLICATIONS

Schräder, "Contrast Media-Induced Renal Failure: and Overview", *Journal of Interventional Cardiology*, vol. 18, No. 6, pp. 417-423 (2005).

\* cited by examiner

COLLECTION CATHETER AND KIT

I. BACKGROUND OF THE INVENTION

1. Field of the Invention

This invention pertains to catheters for collecting fluid from a blood vessel of a patient.

2. Description of the Prior Art

Collection catheters are well known for collecting blood or other fluids from blood vessels of a patient. For example, International Publication No. WO 2005/082440 A1 describes collection catheters for collecting blood from a coronary sinus or other coronary vein in a perfusion system.

In addition to collecting blood in a perfusion process, blood may be collected from a coronary vein in an angiography procedure. Such procedures are used for assessing patency of coronary arteries. These procedures may also be used for other purposes—for example, in stent placement or other procedures. In such a procedure, a contrast medium is injected into a coronary artery proximal to a suspected site of a coronary obstruction.

Contrast media may have significant health risks if permitted to flow systemically to the patient's organs. For example, renal dysfunction or failure may occur from such systemic delivery of a contrast media. Such failure is referred to as "contrast-induced nephropathy" or CIN. Schräder, "Contrast Media-Induced Renal Failure: And Overview", *Journal of Interventional Cardiology*, Vol. 18, No. 6, pages 417-423 (2005).

A number of different techniques in catheter designs have been suggested for collecting contrast media. Examples of such are shown in U.S. Pat. No. 6,554,819 to Reich issued Apr. 29, 2003; U.S. Patent Application Publication No. US 2002/0099254 A1 to Movahed published Jul. 25, 2002; U.S. Patent Application Publication No. US 2005/0256441 A1 to Lotan et al., published Nov. 17, 2005, U.S. Patent Application Publication No. 2005/0124969 to Fitzgerald et al. published Jun. 9, 2005 and U.S. Patent Application Publication No. US 2006/0013772 A1 to LeWinter et al., published Jan. 19, 2006. A contrast removal system is also described in Michishita, et al. "A Novel Contrast Removal System From The Coronary Sinus Using An Absorbing Column During Coronary Angiography In A Porcine Model", *Journal of the American College of Cardiology*, Vol. 47, No. 9 (2006).

Blood collected in a contrast removal or other blood collection system may be processed to be re-admitted to the patient. However, it is more common for collected blood to be discarded. It is generally recognized that a limited amount (e.g., 100 milliliters to 200 milliliters) of blood may be safely removed from a patient and discarded.

Blood collection techniques include methods and apparatus for isolating blood flow in a vessel. This insures that substantially all antegrade flow (i.e., the normal direction of blood flow in a vessel) is collected for a period of time to substantial collect all contrast media or perfusate which is the object of collection.

Importantly, such isolation is employed to avoid collection of retrograde blood flow. Retrograde flow (in a direction opposite normal blood flow in a vessel) may occur, for example, where a catheter draws blood from a coronary sinus under suction. The suction may be such that blood in the right atrium flows retrograde and is drawn through the catheter. As a result, blood not laden with contrast media or perfusate is collected and possibly discarded. Since there are limits on how much blood may be discarded, it is desirable to avoid collecting and discarding blood not laden with contrast media or perfusate.

Isolation is commonly achieved through use of balloon catheters. A balloon is inflated during periods of blood collection to seal against the wall of the blood vessel. Otherwise, the balloon is deflated to be spaced from the blood vessel wall.

During an angiography, contrast media may be injected at multiple times during a procedure. To collect such contrast media, a balloon is repeated inflated and deflated in a manner timed with the injection. However, it is difficult to precisely coordinate the timing of the inflation and deflation with the withdrawal of blood from the catheter. Maintaining occlusion constantly is undesirable since this may lead to venous congestion and shunting of contrast-laden blood from a coronary sinus to the right atrium through collateral veins.

It is an object of the present invention to provide a method and apparatus for collection of a fluid from a blood vessel.

II. SUMMARY OF THE INVENTION

According to a preferred embodiment of the present invention, a method and apparatus are disclosed for collecting fluid from a blood vessel (such as a coronary sinus) of a patient. The method includes use of a catheter in the form of a collection member having an elongated, flexible tubular portion terminating at a distal end. An annular sealing member (e.g., an inflatable balloon in a preferred embodiment) is secured to the tubular member spaced from the distal end. A collection lumen of the tubular portion has a fluid inlet distal to the sealing member. A proximal end of the tubular member is adapted to be connected to a source of suction for applying a suction to the collection lumen. The method includes placing the distal end in a blood vessel with antegrade flow within the vessel flowing in a direction from the distal end toward the sealing member. The sealing member is spaced from opposing surface of the vessel in an absence of a suction applied to the collection lumen. A suction is applied to the collection lumen in an amount sufficient to draw blood from the vessel through the fluid inlet and into the collection lumen and further sufficient to urge the opposing surface of the blood vessel to migrate into sealing engagement with the sealing member.

III. BRIEF DESCRIPTION OF THE DRAWINGS

IV. DESCRIPTION OF THE PREFERRED EMBODIMENT

Referring now to the several drawing figures in which identical elements are numbered identically throughout, a description of a preferred embodiment of the present invention will now be provided.

Figure 1:
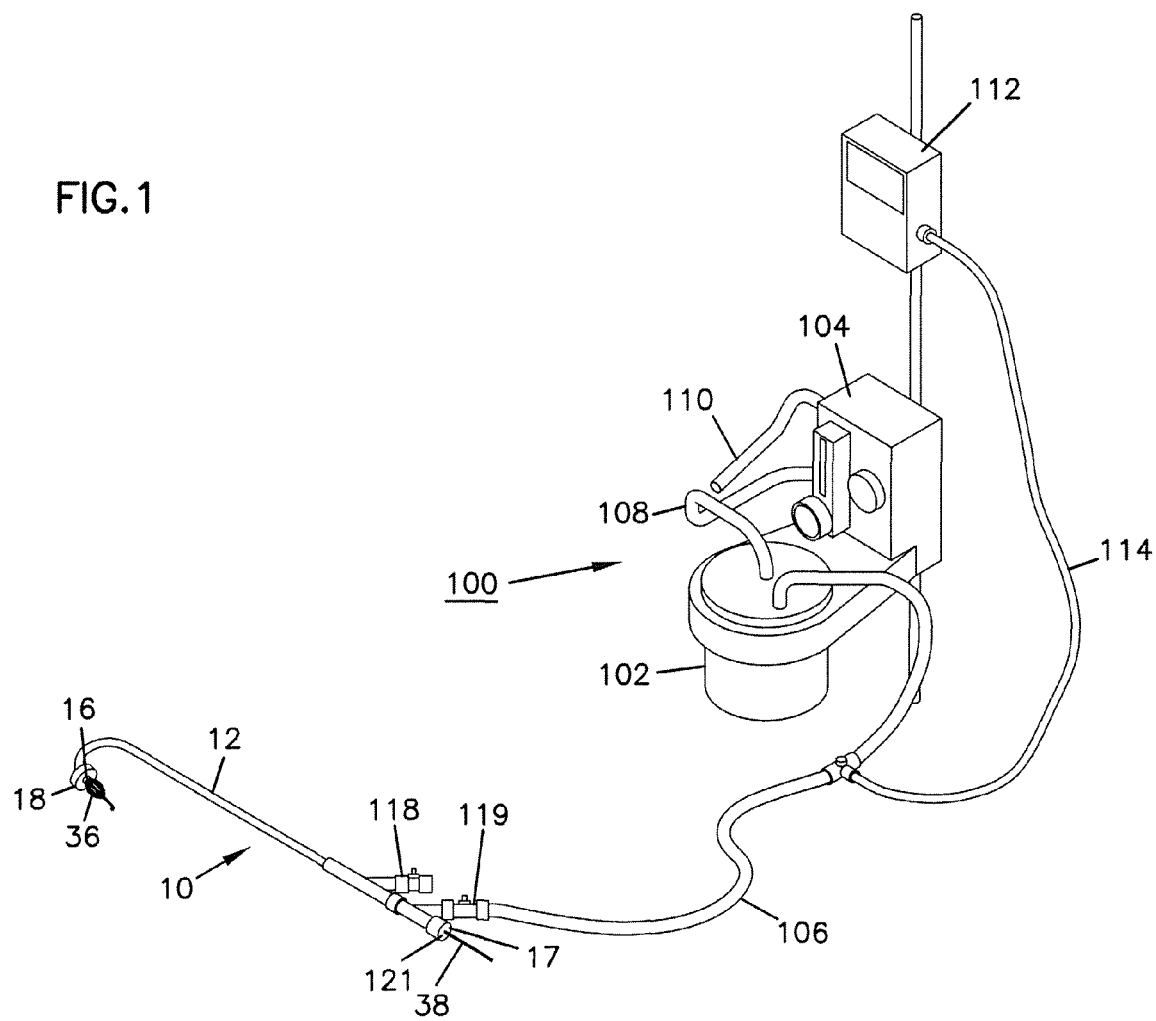
FIG. 1 illustrates a system including a collection catheter according to the present invention for collection of blood from a patient's blood vessel and also showing an optional vessel support apparatus.

FIG. 1 shows a system 100 including a collection catheter 10 according to the present invention. In a preferred embodiment, the collection catheter 10 is used to collect blood flow laden with a perfusate or a contrast media which had been injected into a coronary artery for angiography or similar procedures. The collection catheter 10 is to collect blood flow from the coronary sinus before such blood flow can pass systemically to the remainder of the patient's body. While such is a preferred embodiment, the apparatus of the present invention can be used in any blood collection technique including that described in the aforementioned International Publication No. WO 2005/082440 A1 (incorporated herein by reference) as well as any dialysis or similar blood collection system. Accordingly, the reference to coronary sinus is illustrative only and can include any other blood vessel.

Figure 1A:
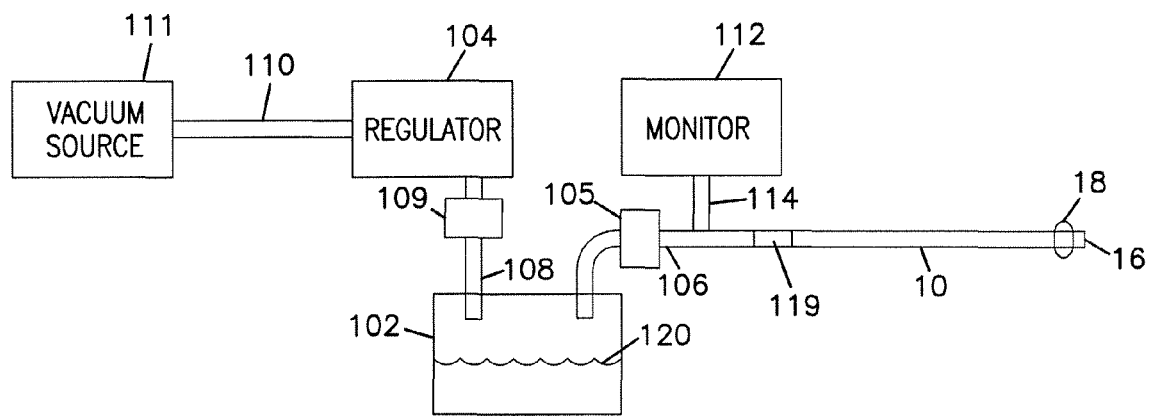
FIG. 1A is a schematic representation of the system of FIG. 1.

In addition to the collection catheter 10, the system 100 includes a collection canister 102 and a vacuum regulator 104. The collection canister 102 is sealed from atmospheric pressure. The system of FIG. 1 is schematically shown in FIG. 1A which also illustrates a level of collected blood within the canister 102 and indicated by 120. Further FIG. 1A shows a trap 109 and a pinch valve 105 as will be described.

Tubing 106 is connects to a port 119 of the collection catheter to communicate with a central lumen 26 (as will be described with reference to FIG. 4) of the collection catheter 10. The tubing 106 connects the collection lumen 26 to the interior of the canister 102.

Tubing 108 connects the interior of the canister 102 to the pressure regulator 104. The pressure regulator 104 has a supply tubing 110 to be connected to a source 111 of a vacuum (FIG. 1A). Such a source is commonly provided in a hospital or other similar setting. FIG. 1A shows a trap 109 for collecting blood which might inadvertently flow toward regulator 104.

The system 100 further includes a pressure monitor 112 connected by a tubing 114 to tubing 106. The pressure monitor 112 monitors and displays the pressure within the tubing 106 thereby corresponding to the pressure within the lumen 26 of the collection catheter 10.

A proximal end 17 (FIG. 1) of the collection catheter 10 also includes a port 118 for connection to the source of pressurized fluid (such as air or saline) for pressurizing a sealing balloon 18 on a distal end 16 of the catheter 10 as will be described. The proximal end 17 also includes a port 121 for passing the support device 30 or a guide wire or the like into the catheter lumen 26.

Figure 2:
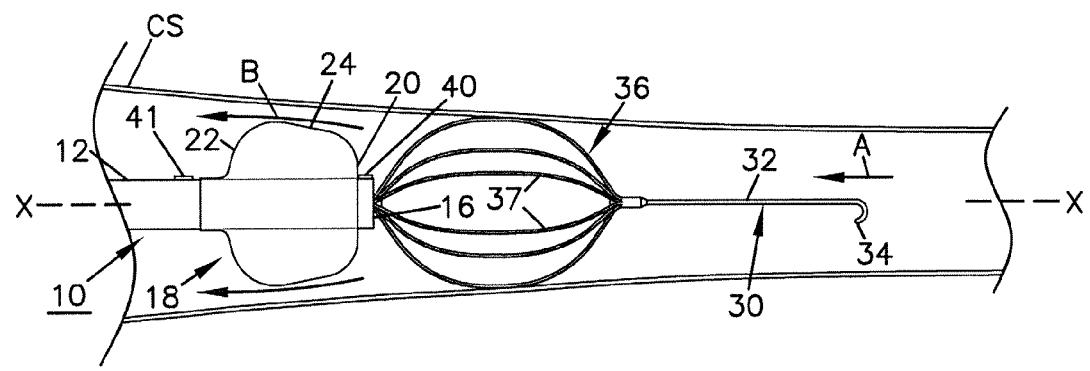
FIG. 2 is a side longitudinal view of a collection catheter of FIG. 1 shown in a coronary sinus of a patient and illustrating spacing between a sealing member and a blood vessel wall when a suction is not applied to a lumen of the catheter.

With best reference to both of FIGS. 1 and 2, the catheter 10 includes a catheter body 12 in the form of an elongated, flexible tubular portion having a proximal end 17 (shown only in FIGS. 1 and 12) and a distal tip 16 (FIG. 2). It will be appreciated that the drawing of FIG. 1 is not to scale and that the length of the catheter body 12 is substantially longer than that shown in FIG. 1 so that the distal tip 16 may be advanced through the vasculature of a patient into a coronary sinus CS while the proximal end 17 remains external to the patient.

As shown in FIG. 2, an annular sealing member 18 is provided in close spacing to the distal end 16. In a preferred embodiment, the annular sealing member 18 is a compliant balloon formed of material which can both conform and stretch as it is inflated. It will be appreciated that compliant balloons are well-known in the art and form no part of this invention per se. Also, the sealing member need not be a balloon. For example, it can be a mechanically actuated sealing surface moved into close spacing from the vessel wall.

In the embodiment of FIG. 2, the balloon has a radial distal end 20 of smaller diameter than a radial proximal end 22. As a result, an annular surface 24 between the ends 20, 22 is inclined relative to a longitudinal axis X-X of the tubular member 12. It will be appreciated that this geometry is illustrative only. If desired, ends 20 and 22 can have a common diameter such that the annular surface 24 is parallel to the axis X-X. Surface 24 can also be curved (convex or concave) relative to axis X-X.

The end 16 is open and communicates with a collection lumen 26 running the length of the catheter body 12. The collection lumen 26 communicates with port 119. An inflation lumen 28 is provided in the wall thickness of body 12 for admitting an inflation fluid into the balloon 18. Inflation lumen 28 communicates with port 118.

In the figures, the catheter 10 is shown used in combination with an optional vessel support device 30. The vessel support device 30 forms no part of this invention per se and may be as more thoroughly described in International Publication No. WO 2005/082440 A1.

The vessel support 30 includes a long flexible distal end 32 with a curved tip 34. The distal end 32 and 34 may be formed in accordance with conventional techniques for forming well-known guide wires to atraumatically advance through a patient's vasculature.

Figure 4:
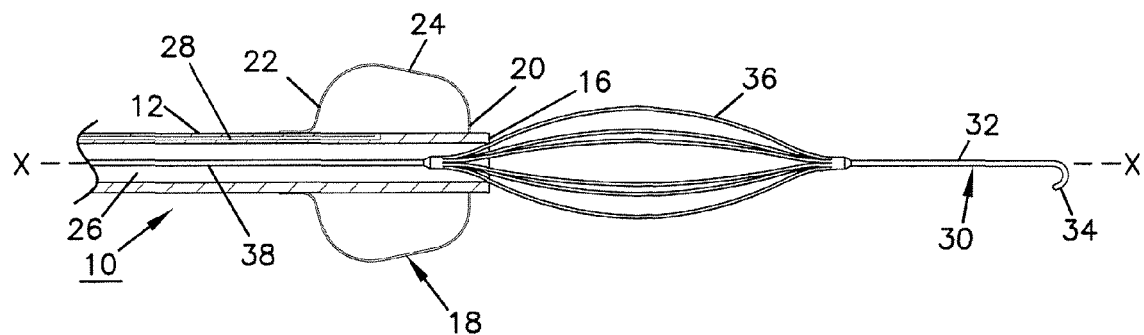
FIG. 4 is a longitudinal side sectional view of the collection catheter and vessel support of FIG. 1.

A support cage 36 connects a distal wire portion 32 to a proximal wire portion 38 (FIG. 4). The cage 36 is made up of a generally circular array (around axis X-X) of flexible elastic struts 37 (such as nitinol or other elastic material suitable for use in a blood vessel). As will become apparent, the cage 36 prevents the collapse of the coronary sinus CS. Further, the positioning of the cage 36 within the coronary sinus provides positioning stability to resist axial movement of the cage 36 relative to the coronary sinus. As a result, the cage 36 is a convenient tool for maintaining a positioning of the catheter 10 within a coronary sinus CS.

In use, a guide wire (not shown) is positioned with a guide wire distal end in the coronary sinus CS at the desired location for collecting blood. Procedures for advancing such guide wires are well known.

Following such guide wire placement, the catheter 10 is advanced over the guide wire until the distal tip 16 is at the desired location for collecting blood. The distal tip 16 may be radiopaque to assess proper placement under fluoroscopy. During advancement, the sealing balloon 18 is fully deflated.

Following such advancement, a physician may inflate the balloon 18. In FIG. 2, normal (or antegrade) blood flow is illustrated by the arrow A indicating a direction of normal blood flow through the coronary sinus CS towards the right atrium (not shown).

The guide wire is then withdrawn and the vessel support 30 is advanced through the catheter 10 into the coronary sinus CS. As soon as the cage 36 passes through the distal end 16, the cage 36 expands to the configuration shown in FIG. 2. With such expansion, the cage 36 abuts opposing surfaces of the coronary sinus CS.

Unlike prior art devices and methods, the balloon 18 is not inflated to such an extent that it abuts against the opposing wall of the coronary sinus CS. Instead, as illustrated in FIG. 2, the balloon 18 is only inflated partially such that an annular flow path is defined between the opposing surfaces of the sealing surface 24 and the coronary sinus CS. This flow path is illustrated by the arrows B in FIG. 2. By way of non-limiting example, the spacing between the sealing surface 24 and the vessel wall may be about 1-2 millimeters.

In the absence of suction applied to the catheter lumen 26, blood flow within the coronary sinus CS flows around the balloon 18 to the right atrium. The catheter lumen 26 may be primed with saline or the like to avoid loss of suction blood flow from the coronary sinus CS into the collection lumen 26.

By monitoring pressure on the pressure monitor 112, a physician can determine if the balloon 18 is over inflated such that it is sealing the coronary sinus CS when no suction is applied to collection lumen 26. If such over inflation is monitored, the balloon 18 may be slightly deflated until the physician is assured that the balloon 18 is residing in the coronary sinus CS in a non-occluding manner. Alternatively, pressure sensors 40, 41 (shown only in FIG. 2) may optionally be provided on catheter body 12 on opposite sides of balloon 18. A pressure differential between sensors 40, 41 indicates occlusion of the coronary sinus CS. Further, either of sensors 40, 41 may be a flow transducer to sensing blood flow over the sensor. Absence of such sensed flow indicates occlusion due to over-inflation of the balloon 18.

Following such placement, the physician may operate the vacuum regulator 104 to generate a suction within the canister 102 and tube 106. The physician selectively applies suction to the catheter lumen 26 by operation of a pinch valve 105 (FIG. 1A) on tube 106. The pinch valve 105 may be a clip or the like which, when opened, permits the vacuum to be applied to the catheter lumen 26. Closure of the pinch valve 105, pinches the tube 106 shut to block the vacuum application to the catheter lumen 26. Accordingly, the application of vacuum to the catheter lumen 26 can be rapidly turned off or on.

Figure 3:
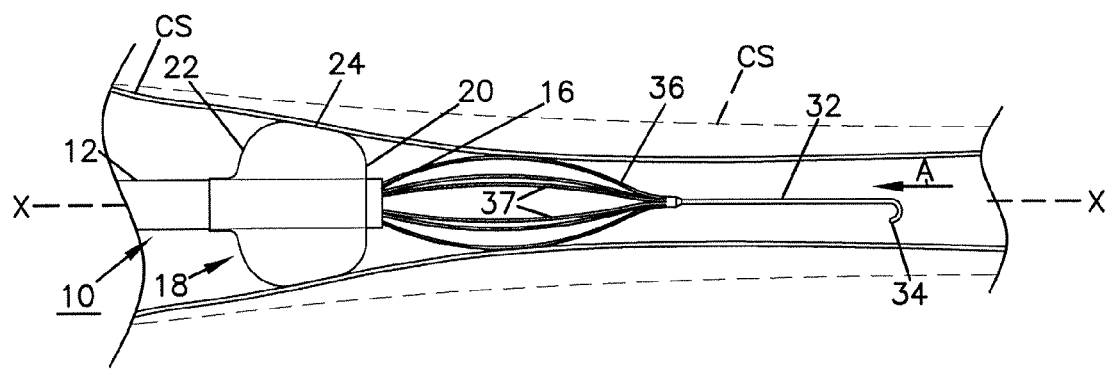
FIG. 3 is the view of FIG. 2 following application of a suction to the lumen of the catheter and illustrating migration of the blood vessel wall into sealing engagement with the sealing member of the catheter.

Application of suction to the catheter lumen 26 causes the coronary sinus CS to at least partially collapse such that the surfaces of the coronary sinus CS opposing the surface 24 migrate against the surface 24 in sealing engagement. This causes blood flow within the coronary sinus CS to flow completely into the lumen 26. Further, such sealing engagement avoids retrograde flow from the right atrium past the balloon 18 to the distal end 16. Such sealing engagement is illustrated in FIG. 3.

The timing of the application of suction to the lumen 26 is preferably timed to result in collection of a contrast media injected into a coronary artery. For example after a set time (about three seconds) after injection of a contrast media into a coronary artery, the suction can be applied to the lumen 26. Alternatively, the patient's electrocardiogram may be monitored and suction may be applied a fixed number (e.g., three) of heart beats following such injection. If desired, a detecting element can be provided at the tip 16 to detect a contrast media resulting in activating application of suction to the lumen 26. For example, pressure sensor 40 in FIG. 2 could alternatively be a contrast media sensor.

Blood drawn into the catheter lumen 26 is collected in canister 102. After collection, the blood may be discarded. Alternatively, the blood may be passed to any suitable treatment apparatus (not shown) for removal of undesired constituents within the collected blood. The treated blood is then returned to the patient.

Figure 3A:
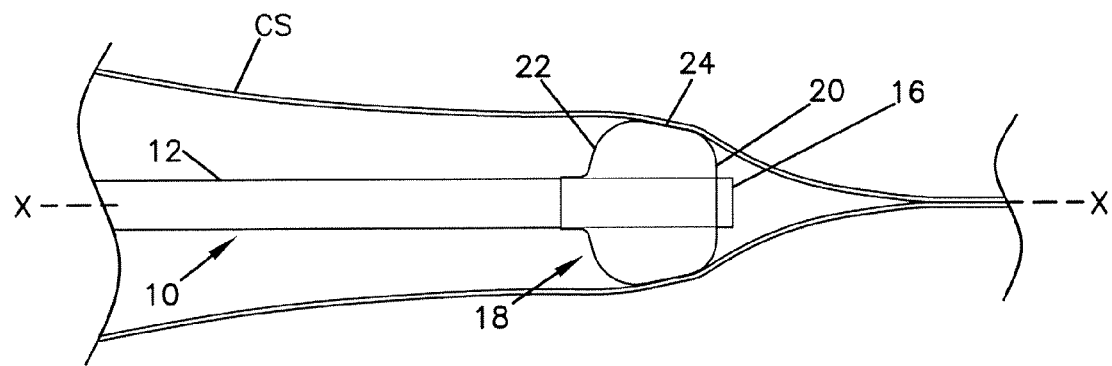
FIG. 3A is the view of FIG. 3 illustrating potential collapse of the blood vessel if not supported distal to the collection catheter.

The amount of suction provided to the lumen 26 is great enough (e.g., a negative 100 millimeters of Hg) to ensure removal of blood from the coronary sinus. The coronary sinus CS is a very fragile and compliant vessel. In response to such suction, the vessel is inclined to collapse. Collapse of the vessel is avoided by the vessel support cage 36. FIG. 3 illustrates the cage 36 distal to the tip 16 preventing complete collapse of the coronary sinus. Instead, cage 36 narrows in diameter (resulting in axial lengthening) but resists complete collapse of the coronary sinus CS. FIG. 3A illustrates potential complete collapse of the coronary sinus CS in the absence of such support.

The tendency of the coronary sinus CS to collapse is utilized as an advantage to result in sealing of the coronary sinus CS against the sealing member 18. As a result, sealing naturally occurs when suction is applied. No additional inflation or deflation of the balloon 18 is required.

Figure 5:
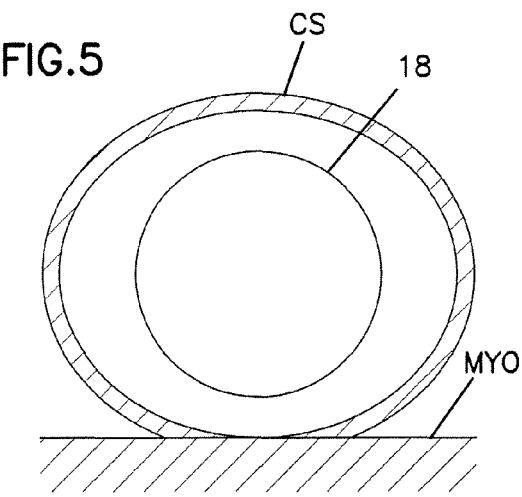
FIG. 5 shows, in cross-section, a sealing member within a coronary sinus and spaced from the walls of the coronary sinus.

In addition to avoiding the need for selective inflation and deflation of the balloon 18, the present invention can achieve better occlusion at lower balloon pressures. This is illustrated in reference to FIGS. 5 and 6. In FIG. 5, the coronary sinus is shown in a rest state (i.e., without application of a suction to the catheter). The sealing member 18 is shown residing within the coronary sinus CS.

The size of a coronary sinus CS may vary significantly from patient to patient. However, in the patient with congestive heart failure the coronary sinus CS may be one to two centimeters in diameter when measured within one to two centimeters of the right atrium.

The reference to the diameter of the coronary sinus CS suggests that the coronary sinus CS is circular in cross section. In fact, the coronary sinus CS is closer to an oval cross section. A portion of the coronary sinus CS is supported by the myocardium (the muscle tissue of the heart). The remainder of the coronary sinus CS is less supported.

Figure 6:
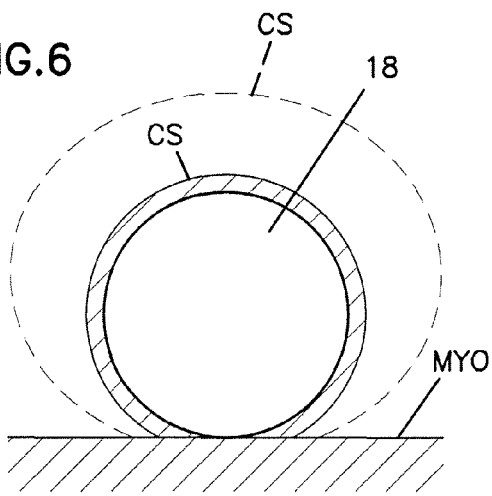
FIG. 6 is the view of FIG. 5 following application of suction to the catheter and showing migration of the wall of the blood vessel against the sealing member.

As a result of differential support of the coronary sinus CS, when a balloon is inflated within a coronary sinus CS, the balloon (which is frequently circular in cross section) is attempting to inflate within and seal against an oval lumen which, due to the variability of surrounding tissue, has variable compliance. By using suction to draw the wall of the coronary sinus CS against the sealing member 18, a more uniform seal is acquired at lower pressure. This is illustrated in FIG. 6, where the rest position of the coronary sinus CS is shown in phantom lines. Solid lines show the coronary sinus CS fully collapsed against the sealing balloon 18.

Figure 7:
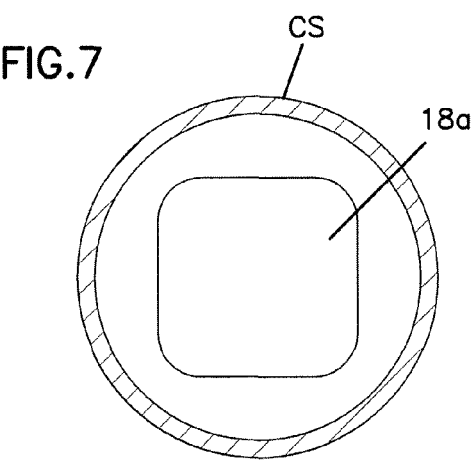
FIG. 7 is the view FIG. 5 and showing an alternative geometry sealing member within a blood vessel prior to application of a suction.
Figure 8:
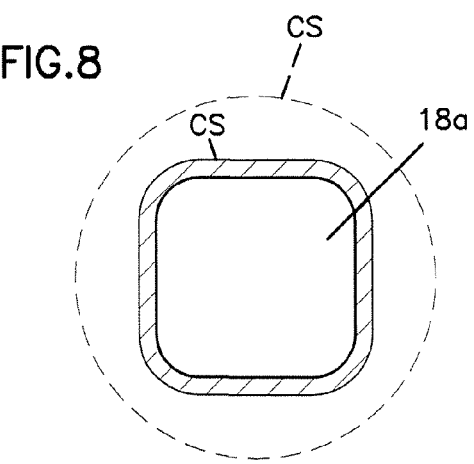
FIG. 8 is the view of FIG. 7 following application of suction.

In FIGS. 5 and 6, the sealing balloon 18 is shown as having a circular cross section. However other geometries can be provided. This is illustrated in FIG. 7 where the sealing balloon 18a is shown as having a generally square cross section. In FIG. 7, the coronary sinus CS is shown circular in cross section for ease of illustration. By reason of the square cross section, a greater cross sectional area is defined between opposing surfaces of the sealing member 18a and the coronary sinus CS. Hence, there is less resistance to blood flow past the balloon 18a when the catheter lumen is not under suction. However, a complete seal is provided following application of suction as illustrated in FIG. 8.

Figure 12:
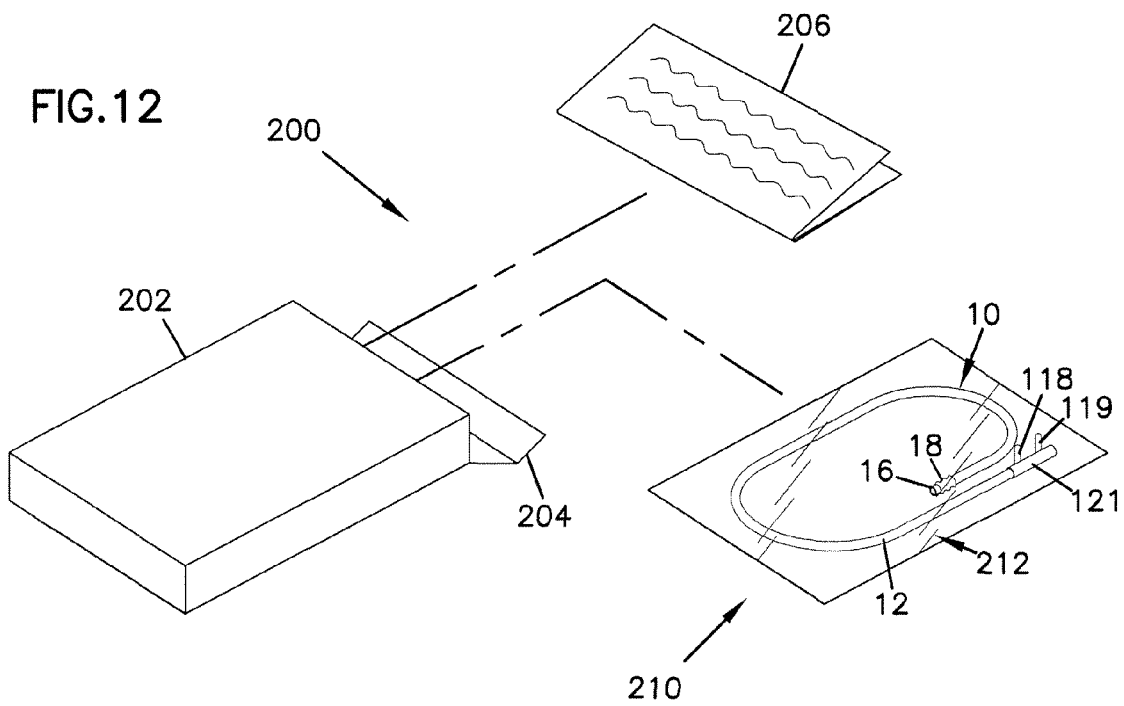
FIG. 12 is an exploded perspective view of a kit according to the present invention.

In a preferred embodiment, the catheter 10 is packaged as a kit 200 shown in FIG. 12. The catheter 10 and its component parts of formed of plastic or other suitable material for placement in human vasculature. The catheter 10 is sized is be advanced through the vasculature with the tip 16 residing in a vein such as a coronary sinus CS. The catheter body 12 is sufficiently flexible and the tip 16 is sufficiently atraumatic to permit such advancement as is known in the art. The materials of the catheter must be appropriate to withstand the rigors of sterilization and meet all biocompatibility requirements as is known in the art.

The catheter 10 is shown in FIG. 12 as contained in a coiled configuration in a clear plastic pouch 212 which is sealed with its contents sterilized for human clinical use. The pouch 212 is contained is a suitable container such as a cardboard box 202 with closure lid 204.

Also contained within the box 202 is a printed sheet 206 containing instructions for use. These instructions 206 include, in at least summary format, the method of the invention described above. Namely, a user is instructed to place the catheter tip 16 in a blood vessel (e.g., coronary sinus CS) with the balloon 18 inflated to be spaced from the vessel wall to permit blood flow past the balloon 18. When desired to collect blood with the catheter 10, suction is applied to the lumen 26 of the catheter 10 to draw the wall of the blood vessel into sealing engagement with the balloon 18.

In FIG. 12, the sterile pouch 212 is shown only containing the collection catheter 10. The kit 200 may contain other system components such as a vessel support 30 and any of tubing 106, 108, 114 or 110.

Figure 9:
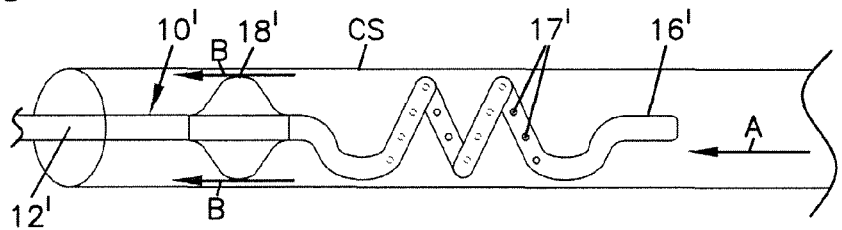
FIG. 9 shows an alternative embodiment of a collection catheter in a blood vessel prior to application of suction.
Figure 10:
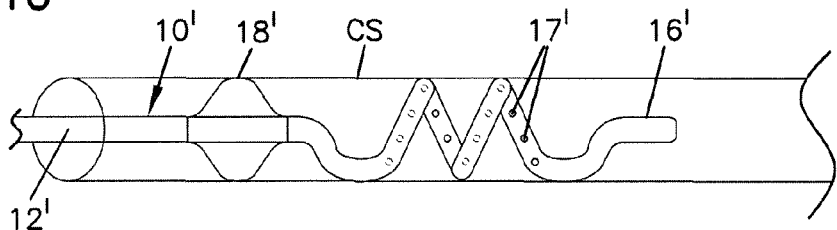
FIG. 10 is the view of FIG. 9 following application of suction.
Figure 11:
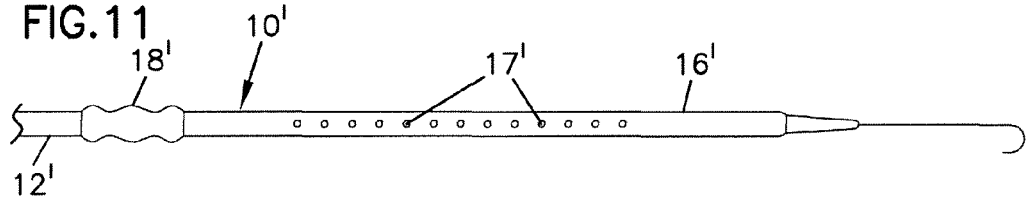
FIG. 11 is the view of the catheter of FIG. 9 shown urged to an uncoiled configuration for advancement through the patient's vascular system.

FIGS. 9-11 illustrate an alternative embodiment of catheter 10'. In the catheter 10', the distal end 16' is shown as an elastomeric material which is biased to a coiled shape (FIGS. 9 and 10). The distal end 16' has a plurality of fluid inlets 17' formed as holes on interior surfaces of the coil. The fluid inlets 17' communicate with the catheter collection lumen.

The balloon 18' is shown spaced from the coronary sinus wall in FIG. 9 indicating that no suction is implied to an interior lumen of the catheter 10'. FIG. 10 shows the apparatus following application of such suction. In FIG. 10, the coronary sinus CS has migrated into sealing engagement with the balloon 18'. Further, the coronary sinus CS has migrated against the external diameter of the coiled portion 16'. As a result, the coiled portion 16' acts to support and prevent collapse of the coronary sinus CS distal to the balloon 18'. This structure avoids the need for the separate vessel support 30 illustrated in use in the embodiments of FIGS. 2-4.

FIG. 11 illustrates that the catheter 10 may be maintained in an elongated state by a guide wire 30'. The guide wire 30' may first be placed within the coronary vasculature and the catheter 10' advanced over the guide wire. Following removal of the guide wire, the bias of the distal end 16' urges the distal end 16' to resume the coil configuration. In FIG. 11, the balloon 18' is shown in a fully deflated state.

Having described the present invention of the preferred embodiment, modifications and equivalents will become apparent to one of ordinary skill in the art. It is intended that such modifications and equivalents be included within the scope of the claims which are appended hereto.

We claim:

1. A method for collecting flow from a blood vessel comprising:
   a. selecting a collection member having:
      i. an elongated, flexible tubular member terminating at a distal end;
      ii. an annular sealing member secured to said tubular member spaced from said distal end;
      iii. a collection lumen with a fluid inlet distal to said sealing member;
      iv. a proximal end adapted to be connected to a source of suction for applying a suction to said collection lumen;
   b. placing said distal end in a blood vessel with antegrade flow within said vessel flowing in a direction from said distal end toward said sealing member and with said sealing member spaced from opposing surface of said vessel in an absence of a suction applied to said collection lumen;
   c. applying a suction to said collection lumen in an amount sufficient to draw blood from said vessel through said fluid inlet and into said collection lumen and further sufficient to occlude said vessel by causing said vessel to radially migrate into sealing engagement with said annular sealing member.

2. A method according to claim 1 wherein:
said tubular member has a longitudinal axis;
said fluid inlet is positioned at said distal end at a plane substantially orthogonal to said longitudinal axis;
said sealing member has an annular sealing surface surrounding said longitudinal axis.

3. A method according to claim 1 wherein a size of said sealing member is selectively adjustable to adjust a spacing between said sealing member and said opposing surface of said blood vessel.

4. A method according to claim 1 further comprising a vessel support distal to said distal end for preventing collapse of said blood vessel in response to said vacuum.

5. The method of claim 1, wherein said annular sealing member has a proximal end, a distal end, and an annular surface extending between said proximal end and said distal end, and wherein said sealing engagement is provided by contact between said opposing surface of said vessel and said annular surface of said annular sealing member.

6. The method of claim 1, further including inflating said annular sealing member within said blood vessel to a predetermined size that provides a spacing between said sealing member and said opposing surface of said blood vessel, wherein said annular sealing member remains at said predetermined size when applying suction to said collection lumen in said amount sufficient to occlude said vessel.

7. The method of claim 1, further including inflating said annular sealing member within said blood vessel to a predetermined size that provides a spacing between said sealing member and said opposing surface of said blood vessel, and wherein said opposing surface of said vessel migrates into sealing engagement with said sealing member when applying said suction to said collection lumen without further inflation of said sealing member.

* * * * *